United States Patent [19]

Klosek et al.

[11] 4,374,297

[45] Feb. 15, 1983

[54] SELECTIVE OXIDATION OF ETHYL TOLUENE OR METHYL STYRENE ISOMER MIXTURES TO ENRICH META-ISOMER CONTENT

[75] Inventors: John M. Klosek, Sewaren; Margaret M. Wu, Belle Mead, both of N.J.

[73] Assignee: Mobil Oil Corporation, New York, N.Y.

[21] Appl. No.: 336,102

[22] Filed: Dec. 30, 1981

[51] Int. Cl.$^3$ .............................................. C07C 7/00
[52] U.S. Cl. .............................. 585/868; 260/687 R; 260/702
[58] Field of Search ............ 585/868; 260/702, 687 R

[56] References Cited

U.S. PATENT DOCUMENTS 3,702,886 11/1972 Argauer et al. ..................... 423/328
3,709,979 1/1973 Chu ..................................... 423/329

Primary Examiner—Delbert E. Gantz
Assistant Examiner—A. Pal
Attorney, Agent, or Firm—Charles A. Huggett; Michael G. Gilman; Edward J. Trojnar

[57] ABSTRACT

The meta isomer content of ethyl toluene or methyl styrene isomer mixtures containing predominately meta isomer and para isomer is increased by subjecting the mixture to oxidation with an oxygen containing gas, e.g. air in the presence of a zeolite modified with a transition metal oxidation catalyst, e.g. Co or Cu ZSM-5. The para isomer is selectively oxidized and the meta isomer is easily separated from the product to give isomer mixtures containing greater than 90 percent meta from mixtures containing 60–65 percent meta and not separable by conventional means.

12 Claims, No Drawings

SELECTIVE OXIDATION OF ETHYL TOLUENE OR METHYL STYRENE ISOMER MIXTURES TO ENRICH META-ISOMER CONTENT

BACKGROUND OF THE INVENTION

1. Field of the Invention

This invention is concerned with selective oxidation of ethyl toluene or methyl styrene isomer mixtures to obtain a product with a high meta isomer content.

2. Description of the Prior Art

Insofar as is now known, it has not been previously proposed to use a modified zeolite to selectively oxidize ethyl toluene or methyl styrene isomer mixtures to obtain a product with a high meta isomer content.

SUMMARY OF THE INVENTION

This invention provides a process for obtaining m-ethyl toluene or m-methyl styrene from a mixture of isomers including p-ethyl toluene or p-methyl styrene that comprises oxidizing a mixture of ethyl toluene or methyl styrene isomers in the presence of a zeolite having a Constraint Index of about 1 to about 12, a silica to alumina mole ratio of at least about 12, and a dried crystal density of not less than about 1.6 grams per cubic centimeter, modified with at least one transition element of the Periodic Chart of the Elements which is effective as an oxidation catalyst.

DETAILED DESCRIPTION OF THE INVENTION

The feed utilized in the process of this invention is a mixture of ethyl toluene or methyl styrene isomer mixtures. One suitable feed is a mixture of methyl styrenes known as "vinyltoluene" which has been commercially available for quite a long time. In general, it is a mixture of about 30–45 weight percent para isomer and about 55–70 weight percent meta isomer. In many polymer applications, this mixture of monomers is not satisfactory. Substantially pure meta or para isomer is more desirable. Another suitable feed is the mixture of ethyl toluene isomers corresponding to "vinyl toluene." When ethyl toluene isomers are converted to products containing a higher meta isomer content in accordance with this invention the product can be dehydrogenated in the known manner to obtain a mixture of methyl styrene isomers rich in the meta isomer and suitable as monomers for polymerization and copolymerization with other monomers to form useful polymers.

In the process of this invention, ethyl toluene or methyl styrene isomer mixtures are selectively catalytically oxidized to increase the meta isomer content. The catalyst used is a zeolite having a Constraint Index of about 1 to about 12, a silica to alumina mole ratio of at least about 12, and a dried crystal density of not less than about 1.6 grams per cubic centimeter, modified with at least one transition element of the Periodic Chart of the Elements which is an effective oxidation catalyst. Elements of Groups VIIA, VIIIA and IB, are particularly suitable. The Periodic Chart of the Elements referred to is published by the Fisher Scientific Company, Cat No. 5-702-10. It is accepted by the International Union for Pure and Applied Chemistry and has been checked by the National Bureau of Standards' Office of Standard Reference Data. Non-limiting examples of suitable transition elements of Groups, VIIA, VIIIA and IB include Co, Cu, Ag, Pd, Fe, Pt and Mn.

Under the conditions utilized in the process of the invention it has been found that the para isomer of ethyl toluene or of methyl styrene is oxidized in preference to the meta isomer resulting in a product with a relatively higher meta isomer to para isomer ratio than the starting material. Since the para isomer is oxidized, to $CO_2$ for example, a high meta isomer product can be easily obtained by removal of the oxidation products by distillation or other means.

Any suitable oxidation conditions can be used in practicing this invention and the oxidation can be conducted batchwise or continuously. It is essential that oxygen be supplied in a molar excess relative to the para-isomer content in the starting isomer mixture. Oxygen can be introduced as such or in mixture with other gases. Preferably, air is used as the oxygen source and sufficient oxygen is available to provide a large molar excess relative to the para isomer. Molar ratios of oxygen to para isomer in the range of 6:1 to 20:1 or even higher are appropriate.

Oxidation is generally conducted at temperatures of about 200° C. to 600° C., preferably 300° C. to 500° C.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tatrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica-alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:
(0–15)RN: (0–1.5)$M_{2/n}O$: (0.2)$Al_2O_3$: (100)$SiO_2$
wherein:
  M is at least one cation having a valence n; and
  RN is a $C_1$–$C_{20}$ organic compound having at least one amine functional group of $pK_a > 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiometry to $2\ RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+(added)/SiO_2$ | = | 0 to 0.2 | 0 to 0.05 | wherein RN is a $C_1$–$C_{20}$ organic compound having amine functional group of $pK_a > 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. This aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pk_a > 7$, as defined above, and includes such compounds as $C_3$–$C_{18}$ primary, secondary, and tertiary amines, cyclic amine (such as piperidine, pyrrolidine and piperazine), and polyamines such as $NH_2$–$C_nH_{2n}$–$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint," which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, Apr. 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The zeolite catalyst of the type described must be modified with a material which is an effective oxidation catalyst. Transition metal compounds particularly members of Groups VIIA, VIIIA and IB such as Mn, $Fe^{(+3)}$, Co, Cu, Pd, Pt and Ag can be applied to the zeolite by soaking the zeolite with a solution, preferably aqueous solution, of the appropriate metal compounds. Suitable compounds include the chlorides, nitrates, acetates, carbonates and amine complexes. The treated catalyst is heated to dry or calcine as described in the following examples. The amount of transition metal compound relative to the zeolite can vary widely. Preferably at least about 0.1 to about 20 percent by weight of the modifying compound based on the zeolite can be used, preferably about 0.5 to 5 weight percent.

The products of this invention are valuable chemical intermediates. For example, meta-methyl styrene is a monomer which can be substituted for styrene as a polymerizable monomer in many applications. Meta-ethyl toluene can be dehydrogenated in the known manner to meta-methyl styrene and used as a monomer as described.

This invention is illustrated by the following non-limiting examples. For the sake of brevity the abbreviations PMS for para methyl styrene and MMS for meta methyl styrene have been used in the examples and tables.

EXAMPLE 1

Preparation of Catalyst, CuZSM-5

2.5 g $NH_4ZSM-5C$ of silica to alumina ratio of 70/1 (crystal size 0.5 micron) was added to a solution containing 0.18 g $Cu(OAc)_2.H_2O$ dissolved in 10 cc hot water. The mixture was allowed to stand for one hour. Then water was stripped off by vacuum to complete dryness.

EXAMPLE 2

Selective Oxidation of PMS in a Mixture Containing Para- and Meta-isomers 2 g of the catalyst, prepared in Example 1 and pelletized to 14/20 mesh size, was mixed with 4 g quartz chips and packed into a quartz down-flow micro-reactor. The catalyst was calcined at 350° C. under stream of air for 2 hours. Then a mixture of methylstyrenes (MS) of PMS/MMS of 35/65 and a stream of air was fed through the reactor. The liquid product was collected through water condenser. The organic layer was analyzed for composition of PMS and MMS. The results are summarized in Table 1.

As these examples show, PMS is selectively removed by oxidation. The resulting liquid product contains high MMS.

EXAMPLE 3

Selective Oxidation of PMS by CoZSM-5

CoZSM-5 was prepared similarly as CuZSM-5 in Example 1, using $Co(OAc)_2.4H_2O$. The catalyst was similarly tested with oxidation of methylstyrenes. The results are summarized in Table 2.

In the first example, pure methylstyrene of 65/35 meta/para was passed through the catalyst with air. In the liquid product, MMS was enriched to 87.5% in methylstyrene fraction. In the second and third examples, a mixture of methylstyrenes and ortho-xylene was fed through the reactor together with air. Again in both examples, the MMS content in methylstyrene fraction is significantly increased. In these examples, ortho-xylene is functioning as an inert internal standard and diluent. The ratios of MMS to ortho-xylene in liquid product remain the same as in starting material.

TABLE 1

| Run No. | Starting Material | 1 | 2 | 3 |
|---|---|---|---|---|
| Temperature °C. | — | 350 | 400 | 500 |
| Feed rate (moles/Hr) | | | | |
| PMS | — | 0.009 | 0.009 | 0.009 |
| MMS | — | 0.017 | 0.017 | 0.017 |
| $O_2$ in air | — | 0.098 | 0.196 | 0.147 |
| Organic Liquid Product Composition (wt %)* | | | | |
| Light Ends | 0 | 5.23 | 1.49 | 1.87 |
| PMS | 35.0 | 1.46 | 3.39 | 16.91 |
| MMS | 65.0 | 91.56 | 94.29 | 80.56 |
| heavies | 0 | 1.75 | 0.81 | 0.63 |
| In Methylstyrene fraction | | | | |
| % PMS | 35.0 | 1.6 | 3.5 | 17.3 |
| % MMS | 65.0 | 98.4 | 96.5 | 82.7 |

*Some aqueous $H_2O$ was collected in the water condenser. In the off gas, $CO_2$ is the only major component.

TABLE 2

| Run No. | Starting Material | 1 | Starting Material | 2 | 3 |
|---|---|---|---|---|---|
| Temperature °C. | — | 350–420 | — | 350–520 | 300–410 |
| Feed Rate Moles/Hr. | | | | | |
| ortho-xylene | — | 0 | — | 0.032 | 0.012 |
| PMS | — | 0.009 | — | 0.013 | 0.005 |
| MMS | — | 0.017 | — | 0.024 | 0.009 |
| air | — | 0.147 | — | 0.196 | 0.147 |
| Organic Liquid Product Composition (Wt. %) | | | | | |
| Light End | 0 | 4.92 | 2.02 | 9.43 | 4.71 |
| ortho-xylene | 0 | 0 | 42.48 | 44.41 | 44.53 |
| PMS | 35.0 | 11.85 | 19.39 | 5.68 | 12.66 |
| MMS | 65.0 | 80.83 | 36.09 | 37.81 | 37.84 |
| heavies | 0 | 2.40 | 0.02 | 2.67 | 0.26 |
| In Methylstyrene fraction | | | | | |
| % PMS | 35.0 | 12.8 | 34.9 | 13.1 | 25.1 |
| % MMS | 65.0 | 87.2 | 65.1 | 86.9 | 74.9 |
| Wt Ratio of | | | | | |

TABLE 2-continued

| Run No. | Starting Material | 1 | Starting Material | 2 | 3 |
|---|---|---|---|---|---|
| MMS/o-xylene | — | — | 0.85 | 0.85 | 0.85 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process for preparing an isomer mixture of ethyl toluene or methyl styrene richer in the meta isomer than the starting mixture which comprises oxidizing a starting mixture of ethyl toluene isomers or methyl styrene isomers containing para isomer in which the meta isomer predominates in the presence of a zeolite having a Constraint Index of about 1 to 12, a silica to alumina ratio of at least about 12 which zeolite is modified with at least one transition element effective as an oxidation catalyst.

2. The process of claim 1 in which said oxidation is conducted in the presence of an oxygen containing gas in a molar excess of the para isomer present.

3. The process of claim 1 in which the starting mixture comprises ethyl toluene isomers containing more than 50 weight percent of the meta isomer.

4. The process of claim 1 in which the starting mixture comprises methyl styrene isomers containing more than 50 weight percent of the meta isomer.

5. The process of claim 1 in which the temperature of oxidation is 200° C. to 600° C.

6. The process of claim 1 in which said modified zeolite is Cu-ZSM-5, Co-ZSM-5, Ag-ZSM-5, Pd-ZSM-5, Fe-ZSM-5, Pt-ZSM-5 or Mn-ZSM-5.

7. The process of claim 1 in which said modified zeolite is Cu-ZSM-5.

8. The process of claim 1 in which said modified zeolite is Co-ZSM-5.

9. The process of claim 1 in which said modified zeolite is Cu-ZSM-11, Co-ZSM-11, Ag-ZSM-11, Pd-ZSM-11, Fe-ZSM-11, Pt-ZSM-11 or Mn-ZSM-11.

10. The process of claim 1 in which said modified zeolite is Cu-ZSM-11.

11. The process of claim 1 in which said modified zeolite is Co-ZSM-11.

12. The process of claim 1 in which a product comprising at least 90 weight percent of the meta isomer is obtained.

* * * * *